United States Patent [19]

Glen et al.

[11] 4,239,776

[45] Dec. 16, 1980

[54] ANTI-ANDROGENIC AMIDES

[75] Inventors: Alasdair T. Glen; Richard W. Bayles, both of Macclesfield, England

[73] Assignee: Imperial Chemical Industries Limited, London, England

[21] Appl. No.: 950,142

[22] Filed: Oct. 10, 1978

[30] Foreign Application Priority Data

Oct. 12, 1977 [GB] United Kingdom ............... 42454/77

[51] Int. Cl.³ .................. A61K 31/275; C07C 121/78
[52] U.S. Cl. ................................ 424/304; 260/465 D
[58] Field of Search ..................... 260/465 D; 424/304

[56] References Cited

U.S. PATENT DOCUMENTS

| | | | |
|---|---|---|---|
| 3,794,683 | 2/1974 | Gassner et al. | 260/562 B |
| 3,875,229 | 4/1975 | Gold | 260/562 R |
| 3,995,060 | 11/1976 | Neri et al. | 424/324 |

FOREIGN PATENT DOCUMENTS 1255161  12/1971  United Kingdom .

OTHER PUBLICATIONS

Grivsky et al., Ind. Chim. Belg., vol. 39, pp. 490–500, (1974).

*Primary Examiner*—Dolph H. Torrence
*Attorney, Agent, or Firm*—Cushman, Darby & Cushman

[57] ABSTRACT

The disclosure relates to novel 3,4-disubstituted-branched-chain-acylanilides, processes for their manufacture and pharmaceutical compositions containing them. The compounds possess anti-androgenic activity. Representative of the compounds disclosed is 3,4-dicyanoisobutyranilide.

8 Claims, No Drawings

ANTI-ANDROGENIC AMIDES

This invention relates to new amides and more particularly it relates to novel acylanilides which possess anti-androgenic properties.

According to the invention there is provided an acylanilide of the formula:

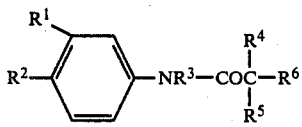

wherein at least one of $R^1$ and $R^2$ is cyano and wherein the other of $R^1$ and $R^2$ is cyano, nitro, trifluoromethyl, chloro, bromo or iodo, or has the formula $-CONR^{11}R^{12}$, wherein $R^{11}$ and $R^{12}$, which may be the same or different, each is hydrogen or alkyl of up to 4 carbon atoms; wherein $R^3$ is hydrogen or alkyl of up to 4 carbon atoms; wherein either $R^4$ and $R^5$, which may be the same or different, each is alkyl of up to 4 carbon atoms, or $R^4$ and $R^5$ are joined together with the adjacent carbon atom to form cycloalkyl of 3 or 4 carbon atoms; and wherein $R^6$ is hydrogen, hydroxy, halogen, alkyl, hydroxy-alkyl or alkoxy each of up to 4 carbon atoms, or acyloxy of up to 15 carbon atoms; provided that when $R^2$ is cyano, $R^3$ and $R^6$ are both hydrogen and $R^4$ and $R^5$ are both methyl, $R^1$ is not chloro.

A suitable value for $R^1$, $R^2$ or $R^6$ when it is halogen is fluoro, chloro, bromo or iodo.

A suitable value for $R^3$, $R^4$, $R^5$, $R^6$, $R^{11}$ or $R^{12}$ when it is alkyl is, for example, methyl or ethyl.

A suitable value for $R^6$ when it is hydroxy-alkyl or alkoxy is, for example, hydroxymethyl, methoxy or ethoxy.

A suitable value for $R^6$ when it is acyloxy is for example, alkanoyloxy of up to 15 carbon atoms, for example acetoxy, propionyloxy, decanoyloxy or dodecanoyloxy.

It will be observed that the acylanilide derivative of the invention may possess an asymmetric carbon atom, namely the carbon atom of the $-CR^4R^5R^6$ group when $R^4$, $R^5$ and $R^6$ are all different, and it may then exist in racemic and optically-active forms. It is to be understood that this invention encompasses the racemic form of such an acylanilide derivative and any optically-active form which possesses anti-androgenic activity, it being a matter of common general knowledge how a racemic compound may be resolved into its optically-active forms and how any anti-androgenic activity present in any of these forms may be determined.

One preferred acylanilide of the invention has the formula stated above wherein $R^1$ is cyano, $R^2$ is cyano, chloro, bromo, iodo or nitro, $R^3$ is hydrogen or alkyl of up to 4 carbon atoms, either $R^4$ is methyl or ethyl and $R^5$ is methyl or ethyl, or $R^4$ and $R^5$ together with the adjacent carbon atom form cyclopropyl, and $R^6$ is hydrogen, hydroxy, chloro, bromo, methyl, hydroxymethyl or methoxy, or alkanoyloxy of up to 12 carbon atoms.

A second preferred acylanilide of the invention has the formula stated above wherein $R^1$ is nitro or trifluoromethyl, $R^2$ is cyano and $R^3$, $R^4$, $R^5$ and $R^6$ have the meanings stated in the last paragraph above.

Specific acylanilides of the invention are hereinafter described in the Examples. Particularly active compounds are 3,4-dicyanoisobutyrylanilide, 3,4-dicyano-(2-hydroxy-2-methylpropionyl)anilide, 3,4-dicyano-N-methylisobutyrylanilide, 3,4-dicyano-(2-methoxy-2-methylpropionyl)anilide and 4-cyano-3-trifluoromethyl-(2-hydroxy-2-methylpropionyl)anilide, and of these the last two are preferred.

The acylanilides of the invention may be manufactured by any chemical process known to be suitable for the manufacture of chemically-analogous compounds.

A preferred process for the manufacture of an acylanilide of the invention comprises the reaction of an amine of the formula

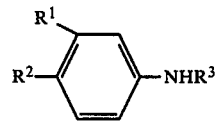

wherein $R^1$, $R^2$ and $R^3$ have the meanings stated above, with an acid of the formula $$HOCOCR^4R^5R^6$$

wherein $R^4$, $R^5$ and $R^6$ have the meanings stated above, or with a reactive derivative of said acid.

A suitable reactive derivative of an acid is, for example, an acid anhydride, or an acyl halide, for example an acyl chloride, or a lower alkyl ester of said acid, for example the methyl or ethyl ester. The reactive derivative may be prepared in situ, for example by reacting the acid with thionyl chloride in a dipolar aprotic solvent such as N,N-dimethylacetamide, hexamethylphosphoric triamide or N-methyl-pyrrolidinone.

An alternative process for the manufacture of an acylanilide derivative of the invention wherein $R^6$ is hydroxy comprises the Smiles' rearrangement of an amide of the formula:

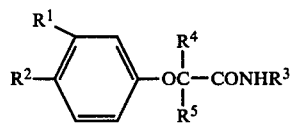

wherein $R^1$, $R^2$, $R^3$, $R^4$ and $R^5$ have the meanings stated above.

The rearrangement may be carried out by treating the amide with a strong base, for example an alkali metal hydride, for example sodium hydride, under anhydrous conditions. The reaction is conveniently carried out at laboratory temperature.

An acylanilide of the invention wherein $R^3$ is alkyl may be prepared by the alkylation of the corresponding acylanilide wherein $R^3$ is hydrogen.

An acylanilide of the invention wherein $R^6$ is acyloxy may be prepared by the acylation of the corresponding acylanilide wherein $R^6$ is hydroxy, and an acylanilide of the invention wherein $R^6$ is hydroxy may be prepared by the hydrolysis of the corresponding acylanilide wherein $R^6$ is acyloxy.

As stated above, an acylanilide of the invention possesses anti-androgenic properties as demonstrated by its ability to decrease the weight of the seminal vesicles and ventral prostate of a castrated male rate when administered concurrently with testosterone propionate. An acylanilide of the invention may therefore be used in the treatment of, for example, malignant or benign prostatic disease or of androgen-dependent disease conditions, such as acne, hirsutism or seborrhoea, in warm-blooded vertebrates including man. It may also be used to improve ovulation in a domestic animal.

The acylanilide of the invention may be administered to a warm-blooded animal in the form of a pharmaceutical or veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for parenteral administration, or be in the form of an ointment or lotion for topical administration, or be in the form of a suppository.

The composition may additionally contain one or more drugs selected from antioestrogens, for example tamoxifen; progestins, for example medroxy-progesterone acetate; inhibitors of gonadotrophin secretion, for example danazol; cytotoxic agents, for example cyclophosphamide; antibiotics, for example penicillin or oxytetracyclin; and anti-inflammatory agents, for example, especially for topical use, fluocinolone acetonide.

The acylanilide of the invention will normally be administered to a warm blooded animal at a dose of between 0.1 mg. and 25 mg. per kg. bodyweight.

The invention is illustrated but not limited by the following Examples:

EXAMPLE 1

Isobutyryl chloride (3 ml.) is added to a stirred solution of 3,4-dicyanoaniline (0.7 g.) in pyridine (15 ml.) and the mixture is stirred at laboratory temperature for 3 hours and then diluted with water (150 ml.). The mixture is extracted with ethyl acetate and the extract is washed with water, dried over magnesium sulphate and evaporated to dryness. The residue is crystallised from a mixture of toluene and petroleum ether (b.p. 60°–80° C.) and there is thus obtained 3,4-dicyanoisobutyrylanilide, m.p. 119°–121° C.

The process described above is repeated except that the appropriate aniline is used in place of 3,4-dicyanoaniline. There are thus similarly obtained the compounds shown in the following table:

$R^2 \underset{R^1}{\underset{|}{\diagup\!\!\!\bigcirc\!\!\!\diagdown}} NHCOCH(CH_3)_2$

| $R^1$ | $R^2$ | m.p.(°C.) |
|-------|-------|-----------|
| cyano | bromo | 146-148 |
| nitro | cyano | 133-135 |
| cyano | chloro | 139-141 |

The process described in the first paragraph above is repeated except that 2-acetoxy-2-methylpropionyl chloride is used in place of isobutyryl chloride. There is thus obtained 3,4-dicyano-(2-acetoxy-2-methylpropionyl)anilide, m.p. 154°–156° C.

EXAMPLE 2

A mixture of 3,4-dicyanoaniline (2 g.) and 2-hydroxy-2-methylpropionic acid (6 g.) is heated at 160° C. for 4 hours and then cooled and shaken with a mixture of ethyl acetate and water. The ethyl acetate layer is separated, washed with dilute aqueous sodium hydroxide solution and then with water, dried over magnesium sulphate and evaporated to dryness. The residue is chromatographed on a silica gel column (200 g.) using a 15% v/v solution of ethyl acetate in chloroform as eluant. The eluate is collected and evaporated to dryness and the residue is crystallised from ethyl acetate. There is thus obtained 3,4-dicyano-(2-hydroxy-2-methylpropionyl)anilide, m.p. 198°–200° C.

EXAMPLE 3

Sodium hydride (100 mg. of a 60% dispersion in mineral oil from which the oil has been removed by washing with petroleum ether b.p. 60°–80° C.) is added to a stirred solution of 2-(3,4-dicyanophenoxy)-2-methylpropionamide (0.5 g.) in N,N-dimethylformamide (10 ml.) which is maintained at 20° C., and the mixture is stirred at this temperature for 30 minutes. Water (100 ml.) is added, the mixture is extracted with ethyl acetate and the extract is washed with water, dried over magnesium sulphate and evaporated to dryness. The residue is crystallised from toluene and there is thus obtained 3,4-dicyano-(2-hydroxy-2-methylpropionyl anilide, m.p. 198°–200° C.

The 2-(3,4-dicyanophenoxy)-2-methylpropionamide used as starting material may be obtained as follows:

Sodium hydroxide (2.25 g.) is added to a solution of 3,4-dicyanophenol (2.0 g.) in acetone (100 ml.), the mixture is heated to 50° C. and a solution of chloroform (1.4 ml.) in acetone (10 ml.) is added dropwise. The mixture is heated under reflux for 5 hours and the acetone is then removed by evaporation. The residue is shaken with diethyl ether and water and the aqueous layer is separated, acidified with aqueous hydrochloric acid and extracted with ethyl acetate. The extract is washed with water, dried over magnesium sulphate and evaporated to dryness. Thionyl chloride (30 ml.) is added to the residue (which consists of 2-(3,4-dicyanophenoxy)-2-methylpropionic acid) and the mixture is heated under reflux for 15 minutes and then evaporated to dryness. The residue is dissolved in dioxan (100 ml.), concentrated aqueous ammonium hydroxide solution (50 ml.) is added and the mixture is stirred at 20° C. for 30 minutes. Water (500 ml.) is added, the mixture is extracted with ethyl acetate and the extract is washed with water, dried over magnesium sulphate and evaporated to dryness. The residue is crystallised from toluene and there is thus obtained 2-(3,4-dicyanophenoxy)-2-methylpropionamide, m.p. 141°–143° C.

EXAMPLE 4

Thionyl chloride (1.5 ml.) is added to a stirred solution of 2-hydroxy-2-methylpropionic acid (2.0 g.) in hexamethylphosphoric triamide (4 ml.) which is cooled to −10° C., and the mixture is stirred at −10° C. for 1 hour. 3,4-Dicyanoaniline (0.3 g.) is added, and the mixture is stirred for 4 hours at laboratory temperature and then diluted with water. The mixture is extracted with ethyl acetate and the extract is washed with water, dried over magnesium sulphate and evaporated to dryness. The residue is dissolved in ethyl acetate and the solution is passed through a short column of silica gel. The eluate is evaporated to dryness and the residue is crystallised from toluene. There is thus obtained 3,4-dicyano-(2-hydroxy-2-methylpropionyl)-anilide, m.p. 198°–200° C.

EXAMPLE 5

The process described in Example 4 is repeated using the appropriate acid and the appropriate aniline derivative as starting materials. There are thus obtained the anilides described in the following table:

$$R^2\text{-}\underset{R^1}{\underset{|}{\bigcirc}}\text{-NH-CO-}\underset{R^5}{\overset{R^4}{\underset{|}{C}}}\text{-}R^6$$

| R¹ | R² | R⁴ | R⁵ | R⁶ | m.p.(°C.) |
|---|---|---|---|---|---|
| cyano | cyano | methyl | methyl | methoxy | 178–180 |
| cyano | cyano | methyl | methyl | hydroxymethyl | 162–164 |
| cyano | cyano | methyl | methyl | bromo | 147–150 |
| cyano | cyano | methyl | ethyl | hydroxy | 142–144 |
| cyano | cyano | ethyl | ethyl | hydroxy | 132–135 |
| cyano | iodo | methyl | methyl | hydroxy | 176–182 |
| trifluoromethyl | cyano | methyl | methyl | hydroxy | 139–140 |

EXAMPLE 6

The process described in Example 1 is repeated except that the appropriate acyl chloride and the appropriate aniline are used as starting materials. There are thus obtained the anilides described in the following table:

$$R^2\text{-}\underset{R^1}{\underset{|}{\bigcirc}}\text{-NH-CO-}\underset{R^5}{\overset{R^4}{\underset{|}{C}}}\text{-}R^6$$

| R¹ | R² | R⁴ | R⁵ | R⁶ | m.p.(°C.) |
|---|---|---|---|---|---|
| cyano | cyano | methyl | methyl | chloro | 171–174 |
| cyano | cyano | methyl | methyl | methyl | 185–187 |
| trifluoromethyl | cyano | methyl | methyl | H | 134–136 |

EXAMPLE 7

Thionyl chloride (0.72 g.) is added dropwise to a stirred solution of cyclopropanecarboxylic acid (0.516 g.) in N,N-dimethylacetamide (15 ml.) which is maintained at −20° C., and the mixture is stirred at that temperature for 1 hour. 3,4-Dicyanoaniline (0.572 g.) is added and the mixture is stirred at laboratory temperature for 16 hours and then diluted with water (50 ml.). The mixture is extracted with ethyl acetate and the extract is washed with water, dried and evaporated to dryness. The residue is crystallised once from toluene and twice from ethyl acetate, and there is thus obtained 3,4-dicyano-(cyclopropanecarbonyl)anilide, m.p. 176°–178° C.

The process described above is repeated except that 2-hydroxy-2-methylpropionic acid and 3-cyano-4-nitroaniline are used as starting materials, and that the crude reaction product is purified by chromatography on a silica gel column using a 1:4 v/v mixture of ethyl acetate and toluene as eluting solvent. The oily product thus obtained is triturated with petroleum ether (b.p. 60°–80° C.) and the solid product thus obtained is crystallised from toluene. There is thus obtained 3-cyano-4-nitro-(2-hydroxy-2-methylpropionyl)anilide, m.p. 148°–152° C.

EXAMPLE 8

3,4-Dicyanoisobutyranilide (0.67 g.) is added to a suspension of sodium hydride (0.11 g. of a 60% dispersion in mineral oil from which the oil has been washed off with petroleum ether b.p. 40°–60° C.) in N,N-dimethylformamide (20 ml.), and methyl iodide (4 ml.) is added after the effervescence has ceased. The mixture is kept at laboratory temperature for 16 hours, water (50 ml.) is added and the mixture is extracted with ethyl acetate. The extract is washed with water, dried and evaporated to dryness and the residue is crystallised from toluene. There is thus obtained 3,4-dicyano-N-methylisobutyranilide, m.p. 122°–123° C.

The process described above is repeated using ethyl iodide or n-butyliodide in place of methyl iodide. There are thus obtained, respectively, 3,4-dicyano-N-ethylisobutyranilide, m.p. 120°–122° C. and N-butyl-3,4-dicyanoisobutyranilide, m.p. 143°–145° C.

EXAMPLE 9

A mixture of 3,4-dicyano-(2-hydroxy-2-methylpropionyl)anilide (0.2 g.), decanoyl chloride (1.5 ml.) and concentrated aqueous hydrochloric acid (0.1 ml.) is heated at 50° C. for 5 hours and then diluted with water. The mixture is extracted with ether and the extract is washed twice with saturated sodium bicarbonate solution, once with water and once with saturated sodium chloride solution, dried and evaporated to dryness. The residue is chromatographed on a silica gel column (10 g.) using a 1:9 v/v mixture of ethyl acetate and toluene as eluting solvent. The product obtained is crystallised from a mixture of ether and petroleum ether (b.p. 40°–60° C.) and there is thus obtained 3,4-dicyano-(2-decanoyloxy-2-methylpropionyl)anilide, m.p. 135°–137° C.

The process described above is repeated except that lauroyl chloride is used in place of decanoyl chloride. There is thus obtained 3,4-dicyano-(2-dodecanoyloxy-2-methylpropionyl)anilide, m.p. 137°–139° C.

EXAMPLE 10

A solution of 3,4-dicyano-(2-acetoxy-2-methylpropionyl)anilide (0.0625 g.) in methanol (5 ml.) is added to a solution of sodium carbonate (0.008 g.) in water (0.5 ml.) and the mixture is stirred at laboratory temperature for 15 minutes and then diluted with water. The mixture is extracted with ether and the extract is washed with water and then with saturated sodium chloride solution, dried and evaporated to dryness. The residue is crystallised from toluene and there is thus obtained 3,4-dicyano-(2-hydroxy-2-methylpropionyl)anilide, m.p. 198°–200° C.

We claim:

1. An acylanilide of the formula:

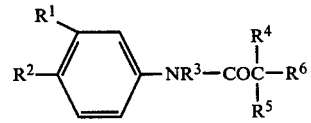

wherein R¹ is cyano, nitro, trifluoromethyl or iodo, or has the formula —CONR¹¹R¹², and wherein R² is cyano, nitro, trifluoromethyl, chloro, bromo or iodo, or has the formula —CONR$^{11}$R$^{12}$, wherein R$^{11}$ and R$^{12}$, which may be the same or different, each is hydrogen or alkyl of up to 4 carbon atoms; wherein R$^3$ is hydrogen or alkyl of up to 4 carbon atoms; wherein either R$^4$ and R$^5$, which may be the same or different, each is alkyl of up to 4 carbon atoms; or R$^4$ and R$^5$ are joined together with the adjacent carbon atom to form cycloalkyl of 3 or 4 carbon atoms; and wherein R$^6$ is hydrogen, hydroxy, halogen, alkyl, hydroxyalkyl or alkoxy each of up to 4 carbon atoms, or acyloxy of up to 15 carbon atoms provided that at least one of R$^1$ and R$^2$ is cyano.

2. An acylanilide as claimed in claim 1 wherein R$^1$ is cyano, R$^2$ is cyano, chloro, bromo, iodo or nitro, R$^3$ is hydrogen or alkyl of up to 4 carbon atoms, either R$^4$ is methyl or ethyl and R$^5$ is methyl or ethyl, or R$^4$ and R$^5$ together with the adjacent carbon atom form cyclopropyl, and R$^6$ is hydrogen, hydroxy, chloro, bromo, methyl, hydroxymethyl or methoxy, or alkanoyloxy of up to 12 carbon atoms.

3. An acylanilide as claimed in claim 1 wherein R$^1$ is nitro or trifluoromethyl, R$^2$ is cyano, R$^3$ is hydrogen or alkyl of up to 4 carbon atoms, either R$^4$ is methyl or ethyl and R$^5$ is methyl or ethyl, or R$^4$ and R$^5$ together with the adjacent carbon atom form cyclopropyl, and R$^6$ is hydrogen, hydroxy, chloro, bromo, methyl, hydroxymethyl or methoxy, or alkanoyloxy of up to 12 carbon atoms.

4. The compound 3,4-dicyanoisobutyrylanilide or 3,4-dicyano-(2-hydroxy-2-methylpropionyl)anilide.

5. The compound 3,4-dicyano-N-methylisobutyrylanilide.

6. The compound 3,4-dicyano-(2-methoxy-2-methylpropionyl)anilide or 4-cyano-3-trifluoromethyl-(2-hydroxy-2-methylpropionyl)anilide.

7. A pharmaceutical or veterinary composition having antiandrogenic properties which comprises an effective amount of an acylanilide, claimed in claim 1, in association with a pharmaceutically-acceptable diluent or carrier.

8. A method of producing an antiandrogenic effect in a warm-blooded animal in need of such an effect which comprises administering to said animal an effective amount of an acylanilide of the formula:

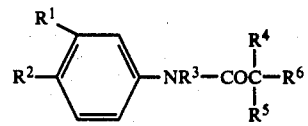

wherein at least one of R$^1$ and R$^2$ is cyano and wherein the other of R$^1$ and R$^2$ is cyano, nitro, trifluoromethyl, chloro, bromo or iodo, or has the formula —CONR$^{11}$R$^{12}$, wherein R$^{11}$ and R$^{12}$, which may be the same or different, each is hydrogen or alkyl of up to 4 carbon atoms; wherein R$^3$ is hydrogen or alkyl of up to 4 carbon atoms; wherein either R$^4$ and R$^5$, which may be the same or different, each is alkyl of up to 4 carbon atoms; or R$^4$ and R$^5$ are joined together with the adjacent carbon atom to form cycloalkyl of 3 or 4 carbon atoms; and wherein R$^6$ is hydrogen, hydroxy, halogen, alkyl, hydroxy-alkyl or alkoxy each of up to 4 carbon atoms, or acyloxy of up to 15 carbon atoms; provided that when R$^2$ is cyano; R$^3$ and R$^6$ are both hydrogen and R$^4$ and R$^5$ are both methyl, R$^1$ is not chloro.

* * * * *